US009775856B2

(12) United States Patent
Grases Santos Silva Rauter et al.

(10) Patent No.: US 9,775,856 B2
(45) Date of Patent: Oct. 3, 2017

(54) C-GLYCOSYLPOLYPHENOL ANTIDIABETIC AGENTS, EFFECT ON GLUCOSE TOLERANCE AND INTERACTION WITH BETA-AMYLOID. THERAPEUTIC APPLICATIONS OF THE SYNTHESIZED AGENT(S) AND OF GENISTA TENERA ETHYL ACETATE EXTRACTS CONTAINING SOME OF THOSE AGENTS

(71) Applicant: FACULDADE DE CIENCIAS DA UNIVERSIDADE DE LISBOA, Lisbon (PT)

(72) Inventors: Amélia Pilar Grases Santos Silva Rauter, Lisbon (PT); Ana Rita Xavier De Jesus, Agualva-Cacém (PT); Alice Isabel Mendes Martins, Paço De Arcos (PT); Catarina Alexandra Dos Santos Dias, Samora Correia (PT); Rogério José Tavares Ribeiro, Almada (PT); Maria Paula Borges De Lemos Macedo, Lisbon (PT); Jorge Alberto Guerra Justino, Santarém (PT); Helder Dias Mota Filipe, Sintra (PT); Rui Manuel Amaro Pinto, Lisbon (PT); Bruno Miguel Nogueira Sepodes, Parede (PT); Margarida Alexandra Patrício Goulart De Medeiros, Santarém (PT); Jesus Jimenéz Barbero, Madrid (ES); Cristina Airoldi, Verderio (IT); Francesco Nicotra, Milan (IT)

(73) Assignee: FACULDADE DE CIENCIAS DA UNIVERSIDADE DE LISBOA, Lisbon (PT)

( * ) Notice: Subject to any disclaimer, the term of this patent is extended or adjusted under 35 U.S.C. 154(b) by 63 days.

(21) Appl. No.: 14/384,145

(22) PCT Filed: Mar. 11, 2013

(86) PCT No.: PCT/IB2013/051916
§ 371 (c)(1),
(2) Date: Sep. 9, 2014

(87) PCT Pub. No.: WO2013/132470
PCT Pub. Date: Sep. 12, 2013

(65) Prior Publication Data
US 2015/0031639 A1 Jan. 29, 2015

(30) Foreign Application Priority Data
Mar. 9, 2012 (PT) .......................... 106202

(51) Int. Cl.
*A61K 31/7048* (2006.01)
*A61K 36/48* (2006.01)

(52) U.S. Cl.
CPC .......... *A61K 31/7048* (2013.01); *A61K 36/48* (2013.01)

(58) Field of Classification Search
None
See application file for complete search history.

(56) References Cited

U.S. PATENT DOCUMENTS 6,482,448 B2 * 11/2002 Tabor .................... A23L 1/2006
424/757

OTHER PUBLICATIONS

Zhao, L., Chen, Q., & Brinton, R. D. (2002). Neuroprotective and neurotrophic efficacy of phytoestrogens in cultured hippocampal neurons. Experimental Biology and Medicine, 227(7), 509-519.*
Babu, P. V. A., Liu, D., & Gilbert, E. R. (2013). Recent advances in understanding the anti-diabetic actions of dietary flavonoids. The Journal of nutritional biochemistry, 24(11), 1777-1789.*
Rauter, A. P. et al. (2005). Liquid chromatography-diode array detection-electrospray ionisation mass spectrometry/nuclear magnetic resonance analyses of the anti-hyperglycemic flavonoid extract of Genista tenera Structure elucidation of a flavonoid/C/glycoside. Journal of Chromatography A, 1089, 59-64.
Edwards, E. L. et al. (2006). Capillary electrophoresis-mass spectrometry characterisation of secondary metabolites from the antihyperglycaemic plant Genista tenera. Electrophoresis, 27(11), 2164-2170.
Reuter, A. P. et al. (2009). Bioactivity studies and chemical profile of the antidiabetic plant Genista tenera. Journal of Ethnopharmacology, 122(2), 384-393.
Rauter, A. P. et al. (2010). Antihyperglycaemic and Protective Effects of Flavonoids on Streptozotocin-Induced Diabetic Rats. Phytotherapy Research, 24, S133-S138.
Ikram, Z. M. et al. (2011). Antidiabetic and hypolipidemic effects of the different fractions of methanolic extracts of *Entada phaseoloides* (L.) MERR. in alloxan induced diabetic mice. *International Journal of Pharmaceutical Sciences and Research*, 2(12), 3160-3165.

(Continued)

Primary Examiner — Shaojia Anna Jiang
Assistant Examiner — Dale R Miller
(74) Attorney, Agent, or Firm — Mark M. Friedman

(57) ABSTRACT

The present invention concerns the antidiabetic-activity of compounds type A, namely of 8-β-D-glucosylgenistein, which is not toxic to eukaryotic cells and has demonstrated to produce complete normalization of fasting hyperglycaemia, to reduce excessive postprandial glucose excursion, to increase glucose-induced insulin secretion and insulin sensitivity. An alternative synthesis for this molecular entity and its binding ability to β-amyloid oligomers is also included in the present invention, which also comprises *Genista tenera* ethyl acetate extract for use as antihyperglycaemic, agent i.e. for lowering blood glucose levels in mammals that are pre-diabetic or have type 2 or type 1 diabetes.
The inhibitory activity of α-glucosidase by *Genista tenera* ethyl acetate and butanol extracts and that of glucose-6-phosphatase by these two extracts and the diethyl ether plant extract is also part of the present invention.

6 Claims, 10 Drawing Sheets

(56) References Cited

OTHER PUBLICATIONS

Melih, O. et al. (2010). Aldose reductase natural inhibitors from ethyl acetate extracts from southern Turkey. *Drug Metabolism Reviews*, 42(51), 170.

International Search Report, mailed Oct. 12, 2013 in connection with PCT International Application No. PCT/IB2013/051916, filed Mar. 11, 2013.

Written Opinion of the International Searching Authority, mailed Oct. 12, 2013 in connection with PCT International Application No. PCT/IB2013/051916, filed Mar. 11, 2013.

* cited by examiner

Scheme 1

Scheme 2

C-GLYCOSYLPOLYPHENOL ANTIDIABETIC AGENTS, EFFECT ON GLUCOSE TOLERANCE AND INTERACTION WITH BETA-AMYLOID. THERAPEUTIC APPLICATIONS OF THE SYNTHESIZED AGENT(S) AND OF *GENISTA TENERA* ETHYL ACETATE EXTRACTS CONTAINING SOME OF THOSE AGENTS

CROSS-REFERENCE TO RELATED APPLICATIONS

This application is a §371 national stage of PCT International Application No. PCT/IB2013/051916, filed Mar. 11, 2013, claiming priority of Portuguese Patent Application No. 106202, filed Mar. 9, 2012, the contents of each of which are hereby incorporated by reference in their entirety.

TECHNICAL FIELD OF THE INVENTION

The present invention comprises new reaction conditions for the synthesis and the application of compounds type A as antidiabetic agents, which interact with beta-amyloid oligomers hence promoting their potential as anti-amyloid aggregation molecular entities.

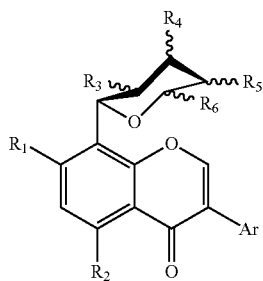

A

Wherein $R_1$, $R_3$, $R_4$ and $R_5$ are the same or different and are hydrogen, alkyl, alkyloxy, amine, amide, alkoxycarbonyl, thioether, thiol, halogens, keto group and $R_2$ is alkyl, alkyloxy, amine, amide, alkoxycarbonyl, thioether, thiol, halogens, keto group or hydrogen, alkyl, alkyloxy, amine, amide, alkoxycarbonyl, thioether, thiol, halogens, keto group and $R_1$ different from R or $R_1$=R but different from hydroxyl with a glucosyl moiety. Wherein $R_6$ is hydrogen, hydroxymethyl, alkyl, alkyloxy, amine, amide, alkoxycarbonyl, thioether, thiol, halogens, keto group Wherein Ar is an aromatic and/or heteroaromatic ring with the formula B, or C

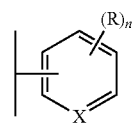

B

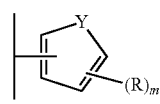

C

Where n is 0-5 and m is 0-3,
Where X is N or C,

Where Y is NR', S, $CH_2$ or O and R' is an alkyl group or hydrogen

When n=1, R is hydrogen, hydroxyl, alkyl, alkanoyl, alkyoxyl, alkoxycarbonyl, amine, amide, nitro, thioether, thiol, halogens, When n≥2, R are the same or different and are hydrogen, hydroxyl, alkyl, alkanoyl, alkyoxyl, alkoxycarbonyl, amine, amide, nitro, thioether, thiol, halogens They show an extensive therapeutical impact on an animal model of beta-cell failure and diabetes and produce complete normalization of fasting hyperglycaemia in streptozotocin (STZ)-induced diabetic Wistar rats. They (or their metabolic products) interfere beneficially on various parameters of glucose and insulin metabolic pathways by increasing glucose-induce insulin secretion, and also insulin sensitivity. The in vitro acute toxicity of the synthesized compounds in eukaryotic cells demonstrated the low toxicity of these antidiabetic molecular entities.

Compounds type I are present in *Genista tenera* ethyl acetate extract, which decreased significantly glycaemia basal levels, inhibited alpha-glucosidase and glucose 6-phosphatase, as well as the butanol extract and the ethyl ether for the latter, and also interacted with beta-amyloid oligomers.

BACKGROUND OF INVENTION

Diabetes mellitus (DM) is a chronic, debilitating and often fatal endocrine disease characterized by a status of hyperglycaemia and eventual glycosuria, caused by the inability of tissues to carry out normal metabolism of carbohydrates. Two forms of DM are usually described: the insulin dependent DM (type 1) and the non-insulin dependent DM (type 2). The first is characterized by a strong deficiency on insulin secretion, associated with auto-immune destruction of pancreatic β-cells. Type 2 DM is caused by a combination of resistance to insulin and impaired insulin secretion, corresponding to more than 90% of cases.

As a result of the long term hyperglycaemia, severe damage of body systems can occur, especially on nerves, blood vessels, heart, eyes, and kidneys conducing to neuropathies, retinopathies, nephropathies and cardiovascular complications. Due to population growth, aging, urbanization, lifestyle alterations and increasing prevalence of obesity, the last two decades have seen an explosive worldwide increase in people diagnosed with DM. According to the last projections from the International Diabetes Federation (IDF) and World Health Organization (WHO) this disease will affect 380 million people in 2025.

DM is becoming the third "killer" of mankind, along with cancer, cardiovascular and cerebrovascular diseases. Because of its prevalence, the WHO has declared DM as an epidemic disease. Although patients can, in most cases, control their glycaemia with the available therapeutically means, together with a correct nutrition, the research of new and effective medicines for the prevention and treatment of this chronic disease is absolutely needed.

Plant Kingdom is a source of bioactive principles against many health problems and a variety of plant metabolites like saponins, alkaloids, flavonoids, anthraquinones, terpenes, coumarins, phenolics, polysaccharides, etc, and plant extracts from a large number of plant families are claimed to possess antidiabetic properties.

Previous research work [4,5,6,7] was developed by the Carbohydrate Chemistry Group of CQB-FCUL [RG-CHEM-LVT-Lisboa-612-640] on the antidiabetic plant *Genista tenera* concerning extracts preparation and the identification of its major constituents: alkaloids and flavonoids. The n-butanol extract of flavonoids revealed a promising antidiabetic activity on an experimental animal model. In vitro toxicity studies of this extract showed no evidence for acute cytotoxicity or genotoxicity. The ethanol extract components were studied with the exception of 8-β-D-glucosylgenistein, which is not commercially available. The components apigenin, chrysoeriol and genistein significantly lowered blood glucose levels of STZ induced diabetic Wistar rats. Hence, synthesis of 8-β-D-glucosylgenistein had to be developed. Sato and coworkers have reported the synthesis of this compound starting from 3,5-benzyl protected phloroacetophenone which glucosylation with benzyl protected glucosyl fluoride in the presence of catalytic amount of $BF_3.OEt_2$ was followed by aldol condensation with benzyl-protected hydroxybenzaldehyde to give a chalcone. Its oxidative rearrangement with thallium (III) nitrate (TTN) and subsequent acid-catalyzed cyclization and debenzylation led to the final product. However, trials to repeat this synthesis were not successful and the reported yields are not reproducible. In addition, the compound has never been reported to be active against diabetes.

Type 2 diabetes, along with other age-related degenerative diseases including Alzheimer's, Parkinson's and Huntington's diseases is related with the accumulation of amyloid fibrils. This accumulation occurs as an outcome of protein mis-folding and consequent intermolecular hydrogen bonding of extended polypeptide strands. According to Glabe, amyloids from different diseases may share a common pathway for fibril formation, since they share common structural properties mainly determined by their generic polymer properties. Soluble amyloid oligomers showed also evidence to be the primary pathogenic structure, rather than the mature amyloid fibrils.

Type 2 diabetes is characterized by islet amyloid deposits derived from islet amyloid polypeptide (IAPP), a protein co-expressed and secreted with insulin by β-cells, and Alzheimer's disease is characterized by the accumulation of β-amyloid (Aβ) fibrils. Both diseases have genetic components, and both their amyloid fibrils form into amyloid aggregates in an aqueous environment. It has been suggested that there might be a relationship between amyloid deposits in the brain and pancreatic islets. Furthermore, a recent study proved that type 2 diabetes is more prevalent in Alzheimer's disease patients, versus non Alzheimer's disease control patients. Presently there is no report on C-glycosylflavonoids which interact with amyloid oligomers.

SUMMARY OF THE INVENTION

The invention is concerned with
a) Flavonoid extract of *Genista tenera* characterized by the fact that the extract is obtained from the aerial parts of the plant and the extraction is performed with ethyl acetate.
b) Flavonoid extract of a) wherein the extract is for use as a medicament and/or a nutraceutic or functional food ingredient.
c) Flavonoid extract of b), wherein the extract is used for treating diabetes.
d) Plant extract of c), wherein the extract is administered in an amount of 60 milligrams or less per kilogram body weight per day, for seven days, to a mammal model.
e) Use of the extract of a) for the preparation of a medicament for the treatment of diabetes type 1 or 2, characterized in that the extract is administered intraperitoneally in a dose of 60 mg/Kg or less of body weight.
f) An antidiabetic composition comprising plant extracts from the genus *Genista*.
g) An antidiabetic composition comprising an ethanol extract of plants from the genus *Genista*.
h) An antidiabetic composition comprising an ethanolic extract of *Genista tenera*.
i) An antidiabetic composition comprising the ethyl acetate flavonoid extract from the ethanol extract of *Genista tenera*.
j) Pharmaceutical composition comprising the plant extracts of a) to i), without hypoglycaemic effects in normoglycaemic animals.
k) Pharmaceutical composition comprising the plant extract of a) to i) that normalizes blood glucose levels on the oral glucose tolerance test (OGTT).
l) A pharmaceutical preparation in dosage unit form adapted for administration to obtain a therapeutic effect, comprising, per dosage unit, a therapeutically effective amount of the plant extract of a) to i).
m) Medical use of the plant extract of a) to e), for treatment of diabetes, wherein a dose of 60 mg/kg or less of body weight is administered.
n) A method for treatment of diabetes comprising the step of administering a quantity of flavonoid extract from *Genista tenera*, to result in a reduction of hyperglycaemia.
o) Pharmaceutical composition comprising ethyl acetate and n-butanol extracts from *Genista tenera* that inhibit the enzyme α-glucosidase, normalizing glucose levels.
p) Pharmaceutical composition comprising diethyl ether, ethyl acetate and n-butanol extracts from *Genista tenera* that inhibits the enzyme glucose-6-phosfatase, normalizing glucose levels.
q) Ethyl acetate extract from *G. tenera* of a) acts as antiamyloidogenic for Alzheimer's disease.
r) Ethyl acetate extract from *G. tenera* of a) acts a new ligand of β amyloid (Aβ) oligomers.
s) Ethyl acetate extract from *G. tenera* of a) acts as a new ligand of Aβ1-42 oligomers.
t) 8-β-d-Glucosylgenistein for the control of glycaemia on a diabetic animal models, both on the fasting and post-load periods.
u) 8-β-D-Glucosylgenistein of t) for the control of glycaemia on a diabetic animal model, both on the fasting and post-load periods.
v) 8-β-D-Glucosylgenistein (4 mg/kg/day or less, 7 days) of t) and u) for the return of basal fasting glycaemia.
w) 8-β-D-Glucosylgenistein (4 mg/kg/day or less, 7 days) of t), u) and v) for the return of post-load glucose excursions to normal control values on rats made diabetic by prior destruction of pancreatic cells with streptozotocin (40 mg/kg).
x) 8-β-D-Glucosylgenistein of t), to interfere beneficially, by itself or by any product of its metabolization, on various parameters of glucose and insulin metabolic pathways.
y) 8-β-D-Glucosylgenistein of t) to x), by itself or by any product of its metabolization, to increase glucose-induced insulin secretion, by direct or indirect interaction with pancreatic cells.
z) 8-β-D-Glucosylgenistein t) to x), by itself or by any product of its metabolization, is able to increase insulin sensitivity, by direct or indirect interaction with peripheral cells, which are mainly, but not exclusively, skeletal muscle myocytes.
  aa) 8-β-D-Glucosylgenistein of t) to x), as a low toxic agent in eukaryotic cells, ten times less toxic than chloramphenicol, when evaluated by the MTT cell viability assay.
  bb) 8-β-D-Glucosylgenistein of t) acts as antiamyloidogenic for Alzheimer's disease.
  cc) 8-β-D-Glucosylgenistein of t) to v) acts a new ligand of β amyloid (Aβ) oligomers.
  dd) 8-β-D-Glucosylgenistein of t) to cc) that acts as a new ligand of Aβ1-42 oligomers.
  ee) Pharmaceutical composition comprising 8-β-D-glucosylgenistein in combination with several flavonoids identified in the ethyl acetate extract of G. tenera.
  ff) Genistein 7-O-β-D-glucoside, present in ethyl acetate extract of G. tenera of a) acting as antiamyloidogenic for Alzheimer's disease.
  gg) Genistein 7-β-D-O-glucoside present in ethyl acetate extract of G. tenera of a) acting a new ligand of β amyloid (Aβ) oligomers.
  hh) Genistein 7-β-D-O-glucoside present in ethyl acetate extract of G. tenera of a) acting as a new ligand of Aβ1-42 oligomers.
  ii) Genistein present in ethyl acetate extract of G. tenera of a) acting as antiamyloidogenic for Alzheimer's disease.
  jj) Genistein present in ethyl acetate extract of G. tenera of a) acting as new ligand of β amyloid (Aβ) oligomers.
  kk) Genistein present in ethyl acetate extract of G. tenera of a) acting as a new ligand of Aβ1-42 oligomers.

DETAILED DESCRIPTION OF THE INVENTION

Figure 1:
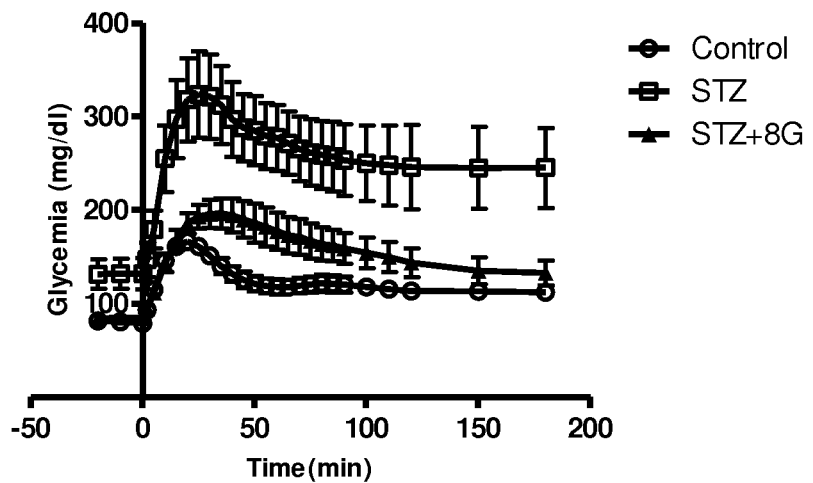
FIG. 1: Glycaemic curves showing basal fasting and post-load (2 mg glucose/kg) values for intragastric glucose tolerance test.
Figure 2:
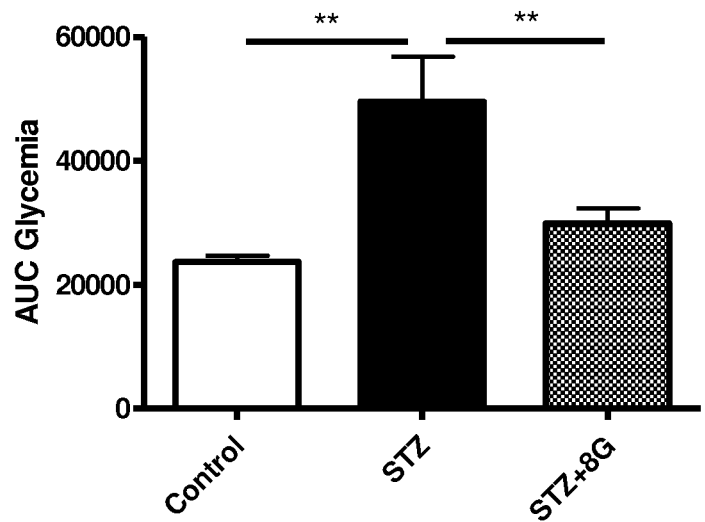
FIG. 2: Area under the curve (AUC) for the glycemic curves for all groups.
Figure 3:
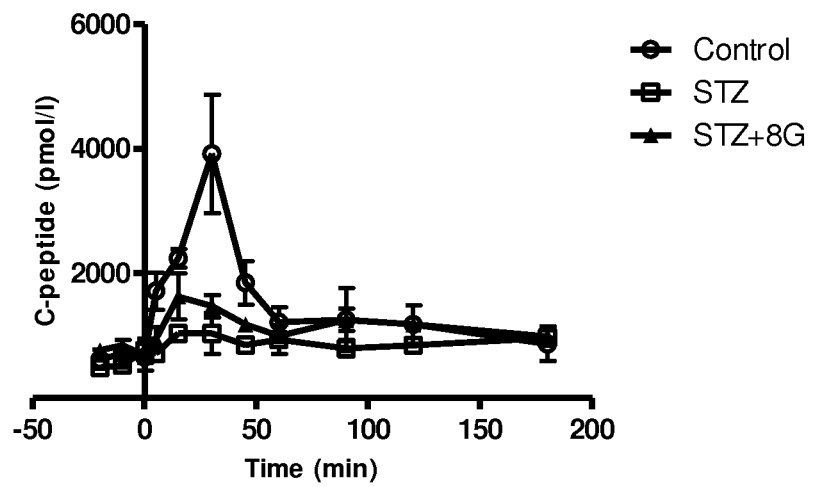
FIG. 3: Dynamic curves for insulin secretion, assessed by c-peptide quantification, during basal fasting and post-load intragastric tolerance test (2 mg glucose/kg).
Figure 4:
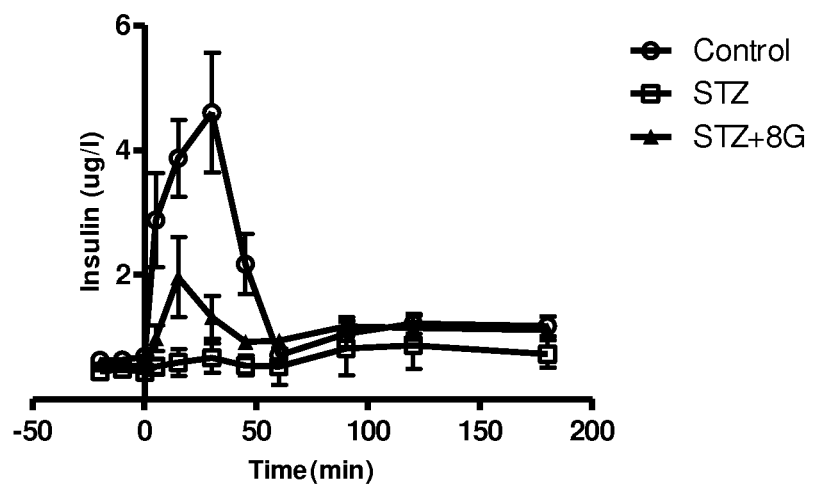
FIG. 4: Dynamic curves for circulating insulin during basal fasting and post-load intragastric tolerance test (2 mg glucose/kg).
Figure 5:
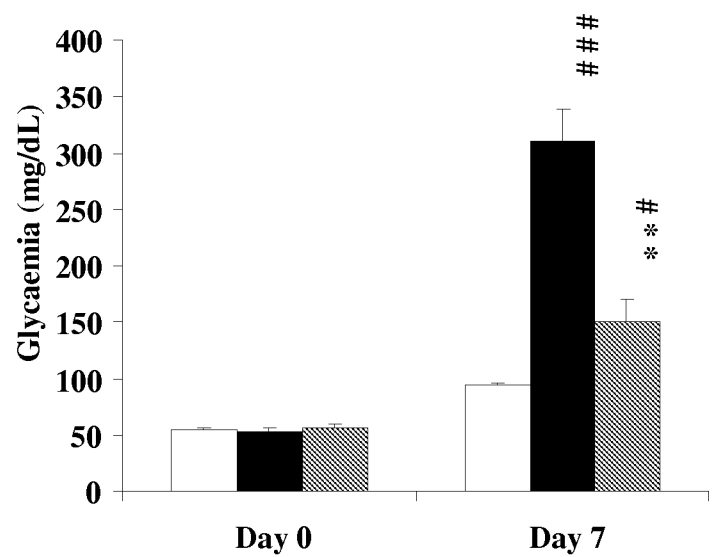
FIG. 5: Antihyperglycemic effect of the extract on diabetic animals (**$P<0.01$ vs STZ; #$P<0.05$; ###$P<0.001$ vs Normal control). White column represents "untreated", n=5; black column represents "treated" with STZ, n=4; and grey column represents "treated" with STZ plus extract, n=5.
Figure 6:
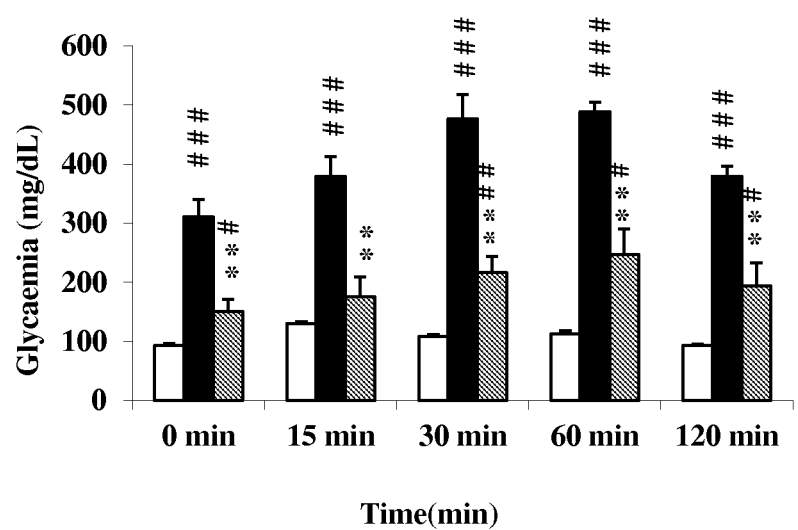
FIG. 6: Effect of the extract on Oral Glucose Tolerance Test (**$P<0.01$ vs STZ; #$P<0.05$; ###$P<0.001$ vs Normal control). White column represents "untreated", n=5; black column represents "treated" with STZ, n=4; and grey column represents "treated" with STZ plus extract, n=5.
Figure 7:
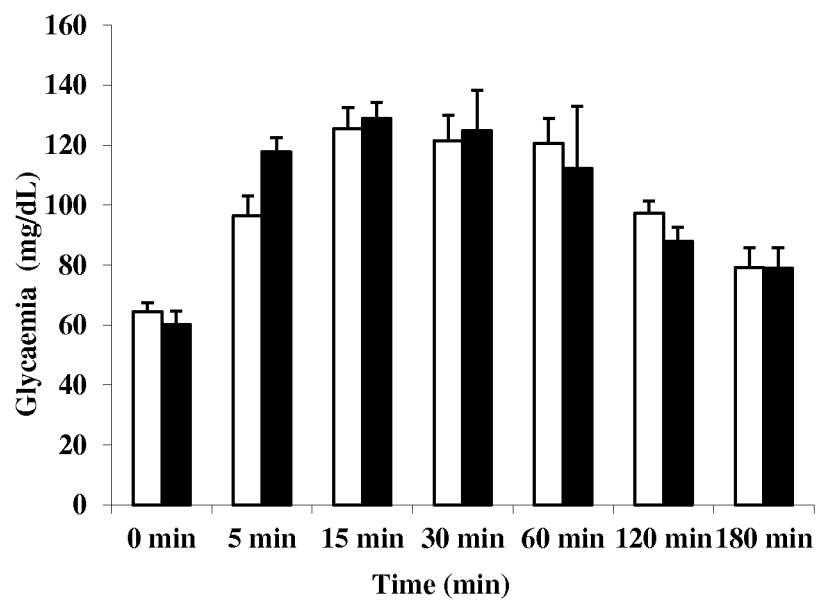
FIG. 7: Effect of the extract on normoglycemic animals.

Diabetes is a growing public health concern and will probably be one of the main medical conditions that need addressing over the next decade. Development of new and nontoxic drugs and functional foods/nutraceuticals to control both diabetes type 1 and type 2 remains a priority area of research. The compound 8-β-D-glucopyranosylgenistein (8-glucosylgenistein, formerly named as genistein 8-C-glucoside) was synthesized via reaction conditions alternative to those reported in the literature. This compound has shown an extensive therapeutical impact on an animal model of beta-cell failure and diabetes. Indeed, a treatment of 7 daily intraperitoneal (i.p.) injections (4 mg/kg each administration) to streptozotocin (STZ)-induced diabetic Wistar rats has demonstrated to produce complete normalization of fasting hyperglycaemia, and a radical amelioration of excessive postprandial glucose excursions to values similar to those observed in healthy normal rats, as given by an intragastric glucose tolerance test. Measurements of circulating insulin and c-peptide were also obtained throughout the glucose tolerance test, to characterize the beneficial effects of the compound on insulin secretion, clearance and action. The synthesized 8-β-D-glucosylgenistein is able to interfere beneficially, by itself or by any product of its metabolism, on various parameters of glucose and insulin metabolic pathways. It is able to increase glucose-induced insulin secretion, by direct or indirect interaction with pancreatic cells, and also insulin sensitivity, by direct or indirect interaction with peripheral cells, which are mainly, but not exclusively, skeletal muscle myocytes.

The in vitro acute toxicity of the synthesized compound in eukaryotic cells was assessed using the MTT cell viability assay. The $IC_{50}$ value was ca. 10 times higher than that of the commercial drug chloramphenicol, demonstrating the low toxicity of this antidiabetic agent.

Compound 8-β-D-glucopyranosylgenistein is the major component of the flavonoids ethyl acetate extract of *Genista tenera*, a plant used in traditional medicine to treat diabetic patients. The entire extract also showed antidiabetic activity. Given daily to STZ Wistar rats (60 mg/Kg/day, i. p.), for 7 days, it induced a significant decrease (52%, P<0.05) of glycaemia basal levels. The protecting effect of the extract was confirmed by the glucose tolerance curve, where a significant decrease of glycaemia was observed 120 min after oral administration (10 mL/Kg) of a 20% glucose aqueous solution. Hypoglycaemic effect of the extract was also evaluated in normoglycaemic animals and animals treated with the extract. The two groups responded similarly to the glucose kinetics in blood for 180 min, proving that the extract does not inhibit glucose transport. These biological properties show the efficacy of this extract for functional foods and nutraceutical purposes, and that of the synthesized compound for more intense drug intervention. Type 2 diabetes, along with other age-related degenerative diseases including Alzheimer's, Parkinson's and Huntington's diseases, is related with the accumulation of amyloid fibrils. This accumulation occurs as an outcome of protein misfolding and consequent intermolecular hydrogen bonding of extended polypeptide strands. Amyloids from different diseases may share a common pathway for fibril formation, since they have common structural properties. Soluble amyloid oligomers show also evidence to be the primary pathogenic structure, rather than the mature amyloid fibrils. Type 2 diabetes is characterized by islet amyloid deposits derived from islet amyloid polypeptide (IAPP), a protein co-expressed and secreted with insulin by β-cells, and Alzheimer's disease is characterized by the accumulation of β-amyloid (Aβ) fibrils. Both diseases have genetic components, and both their amyloid fibrils form into amyloid aggregates in an aqueous environment. The presence of compounds able to bind Aβ1-42 oligomers in ethyl acetate extract of *G. tenera* was investigated by using Saturation Transfer Difference (STD) and tr-NOESY NMR experiments. These experiments unequivocally demonstrate that the extract, 8-β-D-glucosylgenistein and genistein 7-β-D-O-glucoside, the second major constituent of the extract, bind to Aβ oligomers. However the latter suffers intermolecular aromatic-aromatic or carbohydrate-aromatic stacking leading to the formation of a supramolecule, and consequently the C-glucosylgenistein presents a higher affinity to Aβ oligomers than its O-glucoside. Moreover, quantitative NMR techniques confirmed the presence of 8-β-D-glucosylgenistein, in a concentration of 92 mg/g of the ethyl acetate extract of *G. tenera*. Its aglycone is mostly involved in the binding but the glucosyl residue also participates in the interaction process adopting a preferential conformation in which its α-face points towards H2 of the aglycone. Insights on the actual geometry were obtained by using molecular mechanics (MM) calculations, with the MM3* force field, as implemented in the MacroModel program (Maestro Suite). In addition, it was also demonstrated that genistein itself, also a plant component, can act as an Aβ oligomer ligand. These results prove that this plant is a source of bioactive compounds with a potential anti-amyloid aggregation effect, useful in the therapeutics of diabetes and/or Alzheimer's disease (AD) and Aβ1-42 oligomers seem to act as an in vitro model of type 2 diabetes for this type of compounds, supporting the results obtained for the extract and for 8-β-D-glucosylgenistein in the biological assays with STZ-induced diabetic rats.

The ethyl acetate and the butanol plant extracts proved to be more potent than acarbose, a standard drug that inhibits α-glucosidase. In addition, both extracts and the diethyl ether extract inhibited significantly glucose-6-phosphatase, an enzyme acting on gluconeogenesis, a target of therapy for type 2 diabetes, and on glycogenolysis.

Synthesis of Compounds Type A

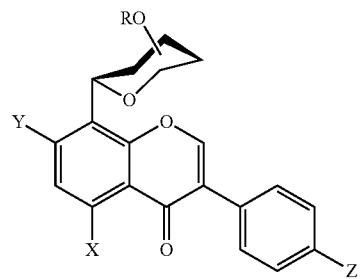

A

Preparation of compound A (X=Y=Z=OH, R=H, sugar residue: glucosyl, 10) was accomplished according to Scheme 1.

Scheme 1 a) 1. DMF, NaH, 30 min., 0° C.; 2. BnBr, 24 h, r.t., 87%; b) AcOH, $H_2SO_4$ 2 N, 24 h, 90-95° C., 81%; c) $Ac_2O$, Py, 1 h, r.t, 96%; d) 1. DMF, $K_2CO_3$, 30 min, 0° C.; 2. BnBr, 1 h, r.t.; e) DCE, Sc(OTf)$_3$, Drierite, 30 min., −30° C. then 5 h, r.t., 49%; f) 1. 1,4-dioxane, aq. NaOH 50% (w/v), 18 h, reflux, 2. $Ac_2O$, Py, DMAP, 1 h, r.t., 60%; g) 1. TIN (III). (MeO)$_3$CH, MeOH, 24 h, 40° C.; 2. THF, MeOH, aq. NaOH 50% (w/v), 4 h, r.t., 63%; h) MeOH, EtOAc, Pd/C, 6 h, r.t., 96%.

The following modifications to the reported methods were used:

A) Benzylation of Acetophloroglucinol

Scheme 2

Synthesis of the starting material 2,4-dibenzyloxy-6-hydroxyacetophenone (6) was successfully accomplished in one single step by benzylation of acetophloroglucinol with BnBr (2 eq.) and $K_2CO_3$ in DMF for 1 h isolated in 69% yield, while the method used by Sato et al.[9] and described by Kumazawa et al synthesized this compound in four steps, reproduced in overall yield of 36%, although reported as 71%. This methodology is more advantageous than the reported in the literature avoiding several protection/deprotection and purification steps.

Example 1

Synthesis of 2,4-dibenzyloxy-6-hydroxyacetophenone (6)

To a solution of 5 (59.6 mmol) in DMF was added $K_2CO_3$ (2.2. equiv.). After stirring for 10 min at 0° C., BnBr (2.2. equiv.) was added and the mixture stirred for 1 h at room temperature.

HCl 2M was added and the mixture was poured into water and extracted with EtOAc. Organic layers were combined, washed with brine, dried over $MgSO_4$ and concentrated. Compound 6 was purified by CC (10:1 hexane/EtOAc) in 69% yield. $R_f$=0.73 (4:1 P. Ether/EtOAc); pf. 103.5-104.0° C. (Lit. [66] p.f.=108-109° C.); $^1$H RMN (CDCl$_3$) δ 14.17 (s, 1H, OH-8); 7.47-7.40 (m, 20H, CH, Ph); 6.22 (d, 1H, $J_{5,7}$=2.32 Hz, H-7); 6.15 (d, 1H. $J_{5,7}$=2.32 Hz, H-5); 5.09 (s, CH$_2$Ph-4); 5.08 (s, CH$_2$Ph-6); 2.61 (s, 3H, H-1); $^{13}$C RMN (CDCl$_3$) δ 203.2 (C-2); 167.6 (C-6 e C-8); 162.1 (C-4); 135.9 (C$_q$-4); 135.7 (C$_q$-6); 128.8; 128.7; 128.5; 128.4; 128.1; 127.7 (CH, Ph); 106.3 (C-3); 94.8 (C-7); 92.4 (C-5); 71.2 (CH$_2$Ph-6); 70.3 (CH$_2$Ph-4); 33.4 (C-1).

B) Glucosylation of 2,4-dibenzyloxy-6-hydroxyacetophenone (6)

Sato and co-workers used glucosyl fluoride as glucosyl donor. When repeating the reported procedure, unidentified byproducts were formed. In alternative, a cleaner reaction was obtained using 1-O-acetyl-2,3,4,6-tetra-O-benzyl-D-glucopyranoside (4) as glycosyl donor and catalytic amount of Sc(OTf)$_3$ as activator. The C-glycosylation of 6 proceeded initially at −30° C. and then at room temperature for 5 h giving product 3 in 49% yield.

Synthesis of 4 in 81% yield was also a clean reaction by treatment of methyl 2,3,4,6-tetra-O-benzyl-α-D-glucoside with AcOH and H$_2$SO$_4$ 2 N at 90-95° C. for 24 h.

Example 2

Synthesis of 3-(2,3,4,6-tetra-O-benzyl-3-D-glucopyranosyl)-4,6-dibenzyloxy-2-hydroxyacetophenone (7)

a) Preparation of the Glucosyl Donor a.1) Synthesis of methyl 2,3,4,6-tetra-O-benzyl-α-D-glucopyranoside (2)

To a 1M solution of NaH in DMF at 0° C. (4.4 eq.) was added dropwise a 1.3 M solution in DMF of methyl D-glucopyranoside (5.14 mmol). The reaction mixture was stirred for 30 minutes at 0° C. and then temperature was allowed to increase to room temperature. BnBr (4.4 eq.) was added dropwise and the stirring continued for more 24 h. MeOH was added (1 mL) and DMF removed. The residue was dissolved in DCM, washed with water and brine. The organic layer was dried over MgSO$_4$ and concentrated. The resulting syrup was purified on a silica gel column (15:1 P. Ether-EtOAc) to give compound 2 (87%) as colorless oil: $R_f$ 0.68 (3:1 P. Ether/ETOAc); $^1$H RMN (CDCl$_3$) δ 7.54-7.31 (m, 20H, CH, Ph), 5.19, 5.17 (part A of AB system, 1H, J=11.13 Hz, CH$_2$Ph), 5.04, 5.01 (part A of AB system, 1H, J=10.86 Hz, CH$_2$Ph), 5.02, 4.99 (part B of AB system, 1H, J=11.26 Hz, CH$_2$Ph), 4.93, 4.90 (part A of AB system, 1H, J=12.21 Hz, CH$_2$Ph), 4.83 (d, 1H, $J_{1,2}$=3.85 Hz, H-1), 4.82, 4.79 (part B of AB system, 1H, J=12.21 Hz, CH$_2$Ph), 4.75, 4.72 (part A of AB system, 1H, J=11.89 Hz, CH$_2$Ph); 4.68, 4.65 (part B of AB system, 1H, J=10.94 Hz, CH$_2$Ph), 4.62, 4.59 (part B of AB system, 1H, J=11.81 Hz, CH$_2$Ph), 4.21 (t, 1H, $J_{3,4}$=9.25 Hz, H-3), 3.94 (ddd, 1H, $J_{5,6a}$=1.73 Hz, $J_{5,6b}$=3.23 Hz, H-5), 3.90-3.78 (m, 3H, H-4, H-6a, H-6b), 3.75 (dd, 1H, $J_{2,3}$=9.67 Hz, H-2), 3.52 (s, 3H, OMe); $^{13}$C RMN (CDCl$_3$) δ 139.9, 138.4, 138.4, 138.1 (Cq, Ph), 128.7, 128.6, 128.6, 128.3, 128.2, 128.1, 128.1, 127.8, 127.9 (CH, Ph); 98.4 (C–1), 82.3 (C-3), 80.0 (C-2), 77.8 (C-4), 75.9, 75.2, 73.7, 73.8 (4 CH$_2$. Ph), 70.2 (C-5), 68.6 (C-6), 55.4 (C, OMe).

a.2) Synthesis of 1-O-acetyl-2,3,4,6-tetra-O-benzyl-D-glucopyranose (4)

To a solution of 2 (9.0 mmol) in AcOH (79.5 mL) was added a solution of H$_2$SO$_4$ 2 N (39.5 mL) and the reaction mixture was stirred at 90-95° C. for 24 h. Cold water (300 mL) was added and the stirring continuing for 30 minutes. A white powder was recrystalized from hot EtOAc, filtered off and washed with hexane and dried in vacuum affording compound 3 in 81% yield.

$R_f$=0.54 (Et.P/EtOAc 3:1), mp. 135.8-137.4° C.; $^1$H RMN (CDCl$_3$) δ 7.37-7.15 (m, 60H, CH, Ph); 5.25 (d, 2H, $J_{1α,2}$=3.52 Hz, H-1α); 4.99-4.50 (m, 25H, H-1β, CH$_2$Ph); 4.43 (t, 1H, $J_{2α,3α}$=8.06 Hz, H-2β); 3.75-3.41 (m, 10H, H-2α, H-3β, H-4β, H-4α, H-5β, H-6 a and b); 4.07 (ddd, 2H, $J_{5α,6aα}$=1.87 Hz, $J_{5α,6bα}$=3.35 Hz, $J_{4α,5α}$=10.01 Hz, H-5α), 4.00 (t, 2H, $J_{3α,4α}$=8.06 Hz, H-3α); $^{13}$C RMN (CDCl$_3$) δ 138.7; 138.2; 137.9; 137.8 (C$_q$, Ph α); 137.8; 137.9; 138.5; 138.4 (C$_q$, Ph β); 128.5; 128.4; 128.4; 128.2; 128.1; 128.0; 127.9; 127.9; 127.8; 127.7; 127.7 (CH$_2$Ph α and β); 97.5 (C-1β); 91.3 (C-1α); 84.6 (C-3α); 83.1 (C-2β); 81.8 (C-3α); 79.97 (C-2α); 77.8 (C-4α); 74.7 (C-4β); 75.8; 75.1; 75.0; 73.5; 73.3 (CH$_2$Ph α); 75.7; 75.1, 74.8; 74.5 (CH$_2$Ph β); 70.25 (C-5α, β); 68.9 (C-6β); 68.6 (C-6α)

Compound 3 was dissolved in pyridine (10 mL/g) and acetic anhydride (5 mL) at room temperature. The mixture stirred for 30 min and pyridine was removed and compound 4 (α/β=3:1) were purified by CC (6:1 P. Ether/EtOAc) in 96% yield. $R_f$=0.79 (3:1 P. Ether/EtOAc); $^1$H RMN (CDCl$_3$) δ 7.42-7.20 (m, 80H, CH, Ph); 6.46 (d, 3H, $J_{1α,2}$=3.32 Hz, H-1α); 5.69 (d, 1H, $J_{1β,2}$=8.13 Hz, H-1β); 5.05-4.53 (m, 32H, CH$_2$Ph); 4.03 (t, 3H, $J_{3α,4α}$=9.27 Hz, H-3α); 3.65-3.84 (m, 14H, H-2α, H-2β, H-3β, H-4α and β, H-5β, H-6 a and b); 3.93-3.97 (m, 1H, H-5α); 2.12 (s, 3H, OCH$_3$β); 2.10 (s, 9H, OCH$_3$α); $^{13}$C RMN (CDCl$_3$) δ 169.5 (CO, Acα); 169.4 (CO, Acβ); 138.7; 138.4; 138.1; 138.0; 137.9; 137.8; 137.6 (C$_q$, Ph α and β); 128.6; 128.5; 128.4; 128.0; 127.9; 127.9; 127.9; 127.8; 127.7; 127.7; (CH$_2$Ph α and β); 94.1 (C-1β); 90.0 (C-1α); 81.7 (C-3α); 81.1 (C-3β); 78.9 (C-2α); 77.0 (C-4α e β); 75.8; 75.5; 75.1; 73.3 (CH$_2$Ph α); 75.8; 75.4; 73.6; 73.6 (CH$_2$Ph β); 75.1 (C-2β); 72.9 (C-5α); 68.1 (C-6α and β); 21.2 (OCH$_3$, Acα); 21.2 (OCH$_3$, Acβ)

B) Glucosylation Reaction

Compounds 4 (2.20 mmol) and 6 (2.0 equiv.) were dissolved in DCE (10 mL) in the presence of drierite (ca. 100 mg). The solution was stirred at −30° C. and Sc(OTf)$_3$ (0.25 equiv.) was added. The stirring continued for 30 min at −30°

C. and then at room temperature for 5 h. The reaction was quenched with water and filtered through celite, extracted with DCM and concentrated. Compound 7 was purified by CC (10:1 P. Ether/EtOAc) and obtained in 49% yield. $R_f$=0.33 (4:1 Et.P./EtOAc); $^1$H RMN (CDCl$_3$) δ 14.54; 14.36 (s cada, 1H, OH-2)*; 7.53-7.00 (m, 30H, CH, Ph); 6.06; 6.01 (s cada, 1H, H-7)*; 5.17-4.31 (m, 13H, CH$_2$Ph, H-1'); 3.91-3.58 (m, 6H, H-2', H-3', H-4', H-5', H-6a' e H-6b'); 2.63; 2.60 (s cada, 3H, H-1)*; $^{13}$C RMN (CDCl$_3$) δ 203.6; 203.4 (C-2)*; 165.1. 165.0 (C-4)*; 164.2; 163.5 (C-6)*; 162.5; 162.3 (C-8)*; 139.1; 138.9; 138.6; 138.5; 138.4; 138.3; 136.2; 135.6; 135.5; ($C_q$. Ph)*; 128.9; 128.9; 128.7; 128.5; 128.4; 128.4; 128.1; 128.0; 127.9; 127.8; 127.7; 127.6; 127.5; 127.3; 127.1; 126.9 (CH. Ph)*; 106.8; 106.7 (C-5)*; 105.9; 105.5 (C-3)*; 89.3; 89.1 (C-7)*; 87.9 (C-3'); 79.8; 79.4 (C-5')*; 78.6; 78.3 (C-4')*; 75.7; 75.5; 75.2; 75.1; 72.8; 72.4; 70.7; 70.1 (CH$_2$Ph); 74.3 (C-2'); 71.1; 70.9 (C-1')*; 69.7 (C-6'); 33.8; 33.7 (C−1)*; * two peaks were observed, corresponding to rotamers as described by Sato et al.

C) Aldol Condensation

Reaction of the C-glucosyl derivative 7 and 4-benzyloxybenzaldehyde with aq. NaOH 50% (w/v) followed by acetylation led to compound 9 in 60% overall yield. These conditions proved to be reproducible while those reported by Sato consisting on treatment with 28% NaOMe-MeOH (solution), followed by stirring at room temperature for 20 h did not result in the expected reaction yield.

Example 3

Synthesis of 1-[2-acetoxy-3-(2,3,4,6-tetra-O-benzyl-β-D-glucopyranosyl)-4,6-dibenzyloxy]phenyl-3-(4-benzyloxyphenyl)prop-2-en-1-one (8)

To a solution of 7 (2.80 mmol) and p-benzyloxybenzaldehyde (1.5 equiv.) in 1,4-dioxane (27.9 mL) was added an aq. solution NaOH 50% (27.9 mL). The reaction mixture was stirred in reflux for 24 h. After this time HCl 2M was added and the mixture was extracted with DCM, washed with brine, dried over MgSO$_4$ and concentrated.

The residue was dissolved in pyridine (10 mL/g residue) and acetic anhydride (2.0 equiv./OH). The mixture was stirred for 30 min and then pyridine was removed. Compound 8 was purified by CC (5:1 P. Ether/EtOAc) in 60% overall yield. $R_f$=0.50 (3:1 P. Ether./EtOAc); $^1$H RMN (CDCl$_3$) δ 7.49-7.21 (m, 38H, CH, Ph, H-3, H-3', H-5'); 6.96 (d, 1H $J_{2',3'}$=8.62 Hz, H-6'); 6.91 (d, 1H $J_{2,3}$=16,15 Hz, H-2); 6.43 (s, 1H, H-5''); 5.14 (s, 2H, CH$_2$Ph-7); 5.04-4.14 (m, CH$_2$Ph, H-1''', H-2'''); 3.91-3.58 (m, H-3''', H-4''', H-5'''; H-6a''', H-6b'''); 2.08 (s, 3H, OCH$_3$, Ac); $^{13}$C RMN (CDCl$_3$) δ 191.9 (C−1); 169.1 (CO. Ac); 160.6 (C-6''); 159.5 (C-1'. C-4'); 157.4 (C-4''); 149.0 (C-2''); 144.9 (C-3); 138.8; 138.6; 138.5; 137.9; 136.5; 136.4 ($C_q$, Ph); 136.0 ($C_q$, Ph-7); 128.7; 128.7; 128.6; 128.5; 128.4; 128.3; 128.2; 128.1; 128.00; 127.9; 127.8; 127.7; 127.6; 127.5; 127.4; 127.3; 127.2; 127.1; 126.9, 126.1 (CH, Ph); 126.2 (C-3', C-5'); 125.9 (C-2); 118.3 (C-1''); 114.9 (C-2', C-6'); 112.8 (C-3''); 96.3 (C-5''); 86.9 (C-3'''); 80.9 (C-2'''); 79.1 (C-5'''); 77.9 (C-4'''); 75.9; 74.9; 73.7; 74.2; 73.2; 71.4; 70.8 (CH$_2$Ph); 73.9 (C-1'''); 69.8 (CH$_2$Ph-7); 68.8 (C-6'''); 20.9 (OCH$_3$).

D) Oxidative Rearrangement

The oxidative rearrangement of chalcones using TTN (III) in methanol was firstly described by Horie et al. The authors suggested that the OH groups in chalcones need to be protected, preferentially by esters such as an acetyl or benzoyl groups, since the hydrogen bond between carbonyl and OH groups interfere in the interaction of the double bond with tallium. Sato and co-workers reported acidic conditions for the cyclization and synthesized compound 9 in only 33% yield. In this invention the reaction was performed in basic conditions using an aqueous solution of NaOH 50%, leading to the formation of perbenzylated C-glucosylisoflavone in 63% yield.

Example 4

Synthesis of 8-(2,3,4,6-tetra-O-benzyl-β-D-glucocopyranosyl)-4',5,7-tribenzyloxyisoflavone (9)

TTN (2.0 eq.) was added to a solution of 8 (1.67 mmol) in (MeO)$_3$CH (45 mL) and MeOH (45 mL). The reaction mixture stirred for 24 h at 40° C. and then sodium bissulfite was added to promote the reduction of Tl (III) to Tl (I). Solid was removed by filtration, water was added and the mixture was extracted with DCM. The combined extracts were dried over MgSO$_4$, filtered off and concentrated.

The yellow residue was dissolved in THF (21 mL) and MeOH (21 mL) and then, aq. NaOH 50% (8.6 mL) was added and the reaction stirred for 4 h at room temperature. After reaction completed HCl 2M was added and the mixture was extracted with DCM, dried over MgSO$_4$, filtered off and concentrated. The residue was separated by CC (5:1 P. Ether) to give 9 in 63% overall yield. $R_f$=0.45 (Et.P/EtOAc, 3:1); $^1$H RMN (CDCl$_3$) δ 7.92 (s, 1H, H-2); 7.54-7.03 (m, 35H, CH, Ph); 6.87 (d, 2H, $J_{2',3'; 5',6'}$=7.23 Hz, H-2', H-6'); 6.78 (d, 2H, H-3', H-5'); 6.43 (s, 1H, H-4); 5.25-4.14 (m, 14H, CH$_2$Ph, H-1''); 3.95-3.60 (m, 6H, H-2'', H-3'', H-4'', H-5'', H-6a'', H-6b'')$^{13}$C RMN (CDCl$_3$) δ 181.8 (C-4), 163.9 (C-7), 162.5 (C-5), 155.7 (C-8a), 152.8 (C-2), 138.5, 138.3, 138.2, 137.8, 136.8, 135.9, 135.8 ($C_q$, Ph), 128.7, 128.6, 128.5, 128.4, 128.3, 128, 2, 128, 1, 128.0, 127.9, 127.8, 127.6, 127.5, 127.3, 127.2, 127.1 (CH, Ph), 122.8 (C-3), 107.7 (C-4a), 104.1 (C-8), 96.94 (C-6), 87.8 (C-2''), 79.6 (C-3''), 78.5 (C-4''), 75.6, 75.2, 75.1, 74.2, 73.5, 73.1, 71.0 (CH$_2$Ph), 74.5 (C-5''), 68.78 (C-6'').

E) Debenzylation

Removal of all benzyl groups of 9 was accomplished with MeOH/EtOAc in the presence of a catalytic amount of Pd/C under hydrogen atmosphere for 2 h at room temperature and compound 10 was obtained in 93% yield. In alternative, Sato9 used 20 wt % of Pd(OH)$_2$/C under H$_2$ atmosphere and the reaction took 5 h at room temperature, giving 94% yield, which confirmed that these conditions are time consuming and do not improve reaction yield.

Example 5

Synthesis of 8-β-D-glucopyranosylgenistein (10)

Pd/C (25 mg) was added to a solution of 9 (0.094 mmol) in MeOH (3 mL) and EtOAc (1 mL) which stirred for at room temperature for 2 h under hydrogen atmosphere. Catalyst was filtered off under celite and washed with MeOH. The filtrate was concentrated and purified by CC (6:1 P. Ether/EtOAc). Compound 10 was obtained in 96% yield. $R_f$=0.35 (1:1 P. Ether/EtOAc); $^1$H RMN (MeOD) δ 8.12 (s, 1H, H-1); 7.37 (d, 2H, $J_{2',3'}$=8.67 Hz, H-2', H-6'); 6.84 (d, 2H, $J_{2',3'}$=8.67 Hz, H-3', H-5'); 6.29 (s, 1H, H-6);

4.95-4.90 (m, 1H, H-1")*; 4.14-4.09 (m, 1H, H-2"); 3.50-3.40 (m, 1H, H-3"); 3.90-3.71 (H-4", H-5", H6a" e H-6b"); $^{13}$C RMN (MeOD) δ 182.7 (C-4); 164.8 (C-7); 163.5 (C-5); 158.9 (C-8a, C-4'); 154.8 (C-2); 131.7 (C-2', C-6'); 124.6 (C-3); 124.3 (C-1'); 116.4 (C-3', C-5'); 105.6 (C-4a); 104.8 (C-8); 97.7 (C-6); 72.9 (C-1"; C-2"); 80.2 (C-3"); 71.9 (C-4"); 82.7 (C-5"); 63.0 (C-6"); *H-1 signal is overlapped with the reference signal of MeOD.

Biological Activity

Activity of 8-β-D-glucopyranosylgenistein (10) on Reducing Excessive Hyperglycaemia We evaluated the ability of the 8-β-D-glucosilisoflavone compound obtained through synthesis to counter the hyperglicaemic state seen on an animal model of diabetes.

Animals

Tests were conducted using male Wistar rats, with weight around 250 g. Animals were maintained under stable conditions of temperature (25° C.), light-dark periods (12 h), and feeding (maintenance rat chow). Both food and water were available ad lib. Food was removed 24 h before testing, to ensure that the animals were on the fasting state. Access to water was maintained during this period.

Induction of Diabetes

A state of hyperglycaemia adequate to the diagnosis of diabetes was induced experimentally through chemical intervention. A sole intraperitoneal (i.p.) injection of streptozotocin (STZ), previously dissolved in saline, was administered at the dose of 40 mg/kg. Hyperglicaemia was checked two days after STZ administration by quantifying glucose on a blood sample collected by tail puncture. The animals on the control group received instead an injection of the same volume of saline, with normoglycaemia checked also after two days.

Experimental Animal Groups

Animals were randomly divided into three groups. Group I (Control) was given one saline injection, and two days after started a 7-days treatment with saline+5% ethanol. This group represents normoglycaemic control. Group II (STZ) was first treated with streptozotocin (40 mg/kg, i.p.) and then for 7 days with saline+5% ethanol. This group represents the diabetic condition. Group III (STZ+8G) was first given STZ (40 mg/kg, i.p.) and then a 7-days treatment with synthesized 8-C-glucosilisoflavone (4 mg/kg/day in saline+5% ethanol, i.p.).

Glucose Tolerance Curve and Associated Insulin Parameters

Animals were anesthetised with sodium pentobarbital (65 mg/kg) after a 24 h fasting period. Immediately after, they were placed on a homoeothermic apparatus. Body temperature was maintained at 37° C. to avoid metabolic changes induced by hypoglycaemia. An exterior loop was surgically placed between the femoral vein and artery, and a catheter was placed on the stomach. After surgery completion, recovery before testing was allowed for a minimum period of 30 minutes. Anaesthesia was maintained throughout the experiment with a constant sodium pentobarbital perfusion on the femoral vein.

Glucose tolerance testing was done first by monitoring blood glycaemia at the fasting state for 20 minutes, after which 2 ml of a glucose solution (2 mg glucose/kg) was administered through the gastric catheter, directly into the stomach. Blood glycaemia was thus measured at regular intervals, by a bench glucose analyzer, both on baseline fasting (from −20 to minutes) and on the post-load period (from 0 to 180 minutes).

Blood samples were also collected for insulin and c-peptide quantification, both at baseline and post-load time points (−20, −10, 0, 5, 15, 30, 45, 60, 90, 120, 180 minutes). These samples were quickly centrifuged and serum was stored at −80° C. for RIA analysis.

Data Analysis

Data is shown as mean±standard error. Mean relates to n observations, in which n represents the number of animals tested (between 5 and 8, depending on the group). Mean values between groups were compared using one-way analysis of variance (ANOVA), followed by a Tukey post-test. Differences were considered statistically significant when $p<0.05$.

Effect of 8-Beta-D-glucopyranosylisoflavone Treatment on Diabetic Animals

STZ administration induced both higher fasting glucose (from 78.8±2.1 on controls, n=5, to 131.8±16.8 mg/dl on STZ, n=5, at minute 0; $p<0.01$) and greater glucose excursions (reaching a maximum of 166.4±3.7 on control and of 323.8±45.9 mg/dl on STZ; $p<0.01$). Post-load endpoint glycaemia, considered here at 180 minutes after gastric glucose loading, was likewise raised (from 112.0±4.3 on control to 245.4±42.8 mg/dl on STZ; $p<0.01$). Total glucose excursion was thus elevated (from an area under the glycaemic curve (AUC) of 23659±990 on controls to 49539±7309 on STZ; $p<0.01$).

These glycaemic parameters were all returned to normal control values on those diabetic rats subjected to the 7-days i.p. administration of 8-C-glucosilisoflavone (4 mg/kg, daily). In this group, n=8, fasting glycaemia obtained was 84.4±3.7 ($p<0.01$ to STZ), maximum post-load glycaemia was 196.5±16.2 ($p<0.01$), and endpoint post-load glycaemia was 132.8±13.3 ($p<0.01$). Total glucose excursion was thus returned to normal (to an AUC of 29865±2484; $p<0.01$ to the STZ group).

In relation to (by chemical destruction of pancreatic cells), STZ administration lead to a decrease on glucose-induced insulin secretion, as estimated through c-peptide insulin parameters, as expected quantification (from an AUC of 287124±37907 on controls to 172261±18480 on STZ; $p<0.05$) and likewise a decrease on circulating insulin (from an AUC of 323.9±50.6 on controls to 137.3±54.4, $p<0.01$). The animals subjected to the short-term treatment with 8-C-glucosilisoflavone showed a partial amelioration of these parameters (insulin secretion: 226892±3972, circulating insulin: 219.0±15.6), however not yet with statistical difference.

These results show that a short-term (7 days) treatment with 8-C-glucosilisoflavone (4 mg/kg/day, i.p.) is able to return fasting glycaemia and post-load glucose excursions to normal, while producing yet a modest amelioration of insulin secretion. This leads to the conclusion that 8-C-glucosilisoflavone is able to also act by increasing insulin sensitivity.

Acute Toxicity of 8-β-D-glucopyranosylgenistein

The potential toxicity of 8-β-D-glucopyranosylisoflavone was evaluated. The in vitro acute toxicity of this compound in eukaryotic cells was assessed using the MTT cell viability assay. The results quantified as IC50 values are summarized in Table 1. Isolated compound showed a low toxic effect, with IC50 values almost 10 times higher than the commercial drug chloramphenicol.

TABLE 1

IC$_{50}$ values of in vitro acute toxicity of the isolated compound of
*Genista tenera* in eucaryotic cells using the MTT cell viability assay.

| | IC$_{50}$ (mg/mL) | StDev |
|---|---|---|
| DMSO | 0.199 | 0.037 |
| H$_2$O$_2$ | 0.002 | 0.002 |
| Chloramphenicol | 0.143 | 0.010 |
| Isolated compound | 1.250 | 0.003 |

MTT Method

Acute cytotoxicity measurements were performed by the MTT method. The 3-(4,5-dimethylthiazol-2-yl)-2,5-diphenyltetrazolium bromide (MTT) assay was used to quantify metabolically viable cells in all samples. Adherent cells (mouse HII4E hepatoma cells) were seeded onto 96-well plates, allowed to attach for 24 h and exposed to the test compound for the following 24 h. Positive control (hydrogen peroxide), negative control (DMSO) and chloramphenicol were also included. At 48 h of culture, MTT was added to the cells at a final concentration of 0.5 mg/mL, followed by an incubation period of 3 h to allow the formazan crystals to form. After incubation, medium was removed, cells were washed twice to remove traces of medium and un-metabolized MTT, and DMSO (100 µL) was added to each well. Solubilisation of formazan crystals was performed by agitation in a 96-well plate shaker for 20 min at room temperature. Absorbance of each well was quantified at 550 nm, using 620 nm as reference wavelength on a scanning multiwell spectrophotometer (automated microplate reader).

Extract Preparation and Biological Activities

Plant Material

Aerial parts of *Genista tenera* were collected in the Island of Madeira, dried in the absence of direct sunlight, and pulverized to form a plant powder.

Extract Preparation

Plant powder was extracted with ethanol 96% (Panreac, VWR), in a Soxhlet extractor. The ethanol extract was concentrated to dryness at low temperature (40° C.) under reduced pressure, in a rotary evaporator Büchi R-200.

The ethanol extract was suspended in hot water (80° C.) and flavonoids extracted sequentially with diethyl ether, ethyl acetate and n-butanol. The tree different extracts were concentrated to dryness in a rotary evaporator Büchi R-200.

This invention concerns to the ethyl acetate extract of flavonoids.

Antihyperglycaemic Activity

The antihyperglycemic activity of the *Genista tenera* flavonoid extract was evaluated in a mammal model.

Administration of the Extract

The extract was dissolved in saline+5% de ethanol (v/v) and administered (60 mg/Kg/day.), for 7 days Animals Adult male Wistar rats, (200-300 g) were used throughout the studies.

Animals were maintained under stable conditions of temperature (25° C.), light-dark periods (12 h), and feeding (maintenance rat chow). Both food and water were available ad libitum. Food was removed 24 h before testing, to ensure that the animals were on the fasting state. Access to drinking water was maintained during this period.

Animals were divided into three groups, each containing 4 to 6 rats:
Group I (Normoglycaemic control)
Group II (Diabetic control)
Group III (Diabetic+Extract)

Experimental Induction of Diabetes

To induce hyperglycaemia, animals were injected intraperitoneally (i.p.) with a single dose (40 mg/Kg) of streptozotocin (STZ) dissolved in saline.

Extract Effect in Diabetic Animals

Animals were divided into three groups:
Group I: Normoglycaemic control (saline+5% ethanol, i.p.),
Group II: Diabetic control (STZ, 40 mg/Kg, saline+5% ethanol, i.p.),
Group III: Diabetic+Extract (60 mg/Kg/day, i.p.)

Extract was given daily, for seven days.

Oral Glucose Tolerance Test (OGTT)

At day 7, it was performed the OGTT assay. Animals received orally (10 mL/Kg) a glucose solution (20%, w/v) and plasma glucose levels were determined at 0 (baseline), 5, 15, 30, 60, and 120 min, with a Glucometer (Accutrend Check, Bohering-Manheim).

Extract Effect in Normoglycaemic Animals

Animals were divided into two groups: control group was injected (i.p.) with the solvent of the extract (saline+5% ethanol), while a second group was treated with the extract (60 mg/Kg, i.p.), 5 min before the OGTT.

Statistical Analysis

Data are shown as mean±standard error. Mean relates to n observations, in which n represents the number of animals tested (4-6). Mean values between groups were compared using the Student's t-test. Differences were considered statistically significant when $P<0.05$.

Fasting glucose levels were significant reduced (c.a. 50%) in diabetic rats treated for seven days with the extract (60 mg/Kg/day, i.p.).

At this dose, after glucose overload (OGTT) no hypoglycaemic activity was observed in normoglycaemic animals treated with the extract.

The extract displays encouraging efficacy in normalizing glucose levels of STZ diabetic rats.

Evaluation of the Antidiabetic Mechanism Shown by the Ethyl Acetate and n-Butanol Plant Extracts The mechanism of the antidiabetic activity of the extracts was evaluated in terms of their inhibitory activity on the enzymes α-glucosidase and glucose-6-phosphatase, which are involved in the metabolism of glucose. The ethyl acetate, n-butanol and diethyl ether were tested, according to the following procedures:

Inhibition of α-Glucosidase

Sample Preparation

The extract samples were firstly dissolved in DMSO, at the concentration of 20 mg/mL. 10 µL of this solution were added to 90 µL of maleate buffer (0.1 M; pH=6.9), being the final tested concentration 400 mg/L.

Inhibitory Assay

Enzyme solutions were prepared using rat intestinal acetone powder (Sigma, St. Louis, Mo., USA) as the source of α-glucosidase. 50 mg of rat intestinal acetone powder were homogenized with 10 mL of 0.1 M maleate buffer at pH 6.9 and centrifuged at 6000×g for 20 min at 4° C. The supernatant obtained before the experiment was used as the enzyme solution for the alpha-glucosidase reaction. The experimental procedure was carried out by the methodology of Mai and coworkers, although with slight modifications. 50 µL of the enzyme solution was pre-incubated with 50 µL of the plant extract solution and 100 µL of 0.1 M maleate buffer (PH 6.9) at 37° C. for 10 min. The enzyme reaction was then started by adding 50 µL of maltose substrate solution (1% w/v in maleate buffer (pH 6.9)). The enzymatic reaction was allowed to proceed at 37° C. for 30 min and then stopped by heating at 100° C. for 5 min.

The generated glucose was quantified with a commercial assay kit (Sigma-Aldrich) at 540 nm. A control was run with 150 µL of maleate buffer 0.1 M (pH=6.9) instead of the extract sample. For blank determination, the enzyme solution was replaced with 0.1 M maleate buffer and the same procedure was carried out as above. Acarbose was tested as reference compound, in a concentration of 400 mg/L. Each extract sample or controls were measured five times. The rate of α-glucosidase inhibition was calculated as a percentage of the control by the formula below:

% inhibition=$(Ac-As)/Ac \times 100$,

Where As is the difference in absorbance decrease at 540 nm between a blank and a sample; Ac is the absorbance of the control. The final concentration of the extract or reference compound for α-glucosidase inhibitory activity was determined under the essay conditions and was expressed as mg/L.

Statistical Analysis

Mean values between groups were compared using one-way analysis of variance (ANOVA), followed by a Tukey post-test. Differences were considered statistically significant when $p<0.05$. Statistical analysis was performed using the Statistical program, version 6.0.

The ethyl acetate and n-butanol extracts revealed a significant α-glucosidase inhibition (enzymatic activity reduced to 2.36% and 0.97%, respectively) being these two extracts much more effective than the standard drug acarbose, which reduced the enzymatic activity to 17.39%.

Inhibition of Glucose-6-Phosphatase

Sample Preparation

The extracts samples were firstly dissolved in DMSO, at the concentration of 20 mg/mL. 40 µL of this solution were added to 60 µL of HEPES 10 mM (0.1 M; pH=6.5), being the final tested concentration 400 mg/L.

Inhibitory Assay

Enzymatic solution was prepared with rabbit liver microsomes as a source of glucose-6-fosfatase as described previously. The microsomal protein (16.74 mg) was resuspended in 0.837 mL HEPES (5 mM, pH 6.5) containing 0.25 mM sucrose, and 1 mM MgCl2, and frozen at −80° C. until use.

Enzymatic assays were performed by the method described by Burchell et al. with some modifications.

Briefly, the G-6-Pase assay was carried out in a final volume of 100 µL with 5 mM glucose-6-phosphate (G-6-P), 2 mM EDTA, 16 mM HEPES pH 6.5 (solution A) and the enzyme.

The reaction was carried out at 37° C. for 60 min without shaking, and stopped by the addition of 1 mL of sulphuric acid (0.33 M), 0.28% ammonium molybdate, 1.11% SDS and 1.11% ascorbic acid (solution B).

The reaction was incubated at 47° C. for 20 min and the absorption recorded in a Shimadzu UV-1700, at 820 nm. In order to study the effect of each extract, it was added to the G-6-Pase assay at a final concentration of 400 mg/mL.

The final concentration of DMSO in control and experimental assays was 2.0%. Phlorizin, dissolved in DMSO (10%) was used at the same concentration of the extracts, as a positive control.

Statistical Analysis

Mean values between groups were compared using one-way analysis of variance (ANOVA), followed by a Tukey post-test. Differences were considered statistically significant when $p<0.05$. Statistical analysis was performed using the Statistica program, version 6.0.

The ethyl acetate, n-butanol and diethyl ether extracts from *Genista tenera* revealed some inhibition of the glucose-6-phosphatase enzyme at the catalytic unit and, eventually, at the Ti transporter. These results are very interesting, once they suggest that the extracts can play a role on the decreasing of the hepatic glucose production, which may be important to the control of type 2 diabetes.

Binding Properties of 8-β-D-Glucopyranosylgenistein, Genistein 7-O-Glucoside, Genistein and the Ethyl Acetate Extract with Beta-Amyloid Oligomers The presence of compounds able to bind Aβ1-42 oligomers in ethyl acetate extract of *G. tenera* was investigated by using NMR experiments, as described below:

Sample Preparation

A batch of Aβ1-42 was selected that contained pre-amyloidogenic seeds highly toxic to N2a cells. The selection was made through sample characterization by NMR spectroscopy, as previously described Immediately before use, lyophilized Aβ1-42 was dissolved in 10 mM NaOD in $D_2O$ at a concentration of 160 µM, then diluted 1:1 with 10 mM phosphate buffer saline, pH 7.4 containing 100 mM NaCl (PBS) and ethyl acetate extract of *G. tenera* or one of the tested compounds. In particular, the final concentrations/quantities of Aβ1-42, genistein-8-C-glucoside, genistein-7-O-glucoside, genistein and the ethyl acetate extract of *G. tenera* in the samples were 80 uM, 2 mM, 1 mM, 1 mM and 3 mg respectively. The pH of each sample was verified with a Microelectrode (Mettler Toledo) for 5 mm NMR tubes and adjusted with NaOD and/or DCl. All pH values were corrected for isotope effect.

For the quantitative NMR experiment, 1.5 mg of ethyl acetate extract of *G. tenera* was dissolved in 550 µL of $D_2O$ and DSS was added to the final concentration of 0.4 mM.

Molecular Mechanics (MM) Calculations

Molecular mechanics were conducted with MacroModel 9.8.207 as implemented in version 9.1.207 of the Maestro suite, using the MM3* force field. A systematic variation of the torsional degrees of freedom of the molecules permitted generating different starting structures that were further minimized to provide the corresponding local minima. Only the same two minima were always found for each molecule (0- and C-glucosides). The continuum GB/SA solvent model was employed and the general PRCG (Polak-Ribiere Conjugate Gradient) method for energy minimization was used. An extended cut-off was applied.

NMR Spectroscopy Binding Studies

NMR experiments were recorded on a Varian 400-MHz Mercury instrument. The basic VARIAN sequences were employed for 2D-TOCSY, 2D-NOESY, $^{13}$C-HSQC, DOSY and STD experiments. For STD, a train of Gaussian-shaped pulses each of 50 ms was employed to saturate selectively the protein envelope; the total saturation time of the protein envelope was adjusted by the number of shaped pulses and was varied between 3 s and 0.3 s. A $^1$H spectrum was acquired with a recycle delay of 60 s to achieve the complete relaxation of all the resonances at each scan. The quantification was performed by comparing the DSS methyl resonance integral with the 8-β-D-glucopiranosylgenistein aromatic resonance integrals.

Binding Properties of the Ethyl Acetate Extract

Upon addition of the Aβ1-42 oligomers to the NMR tube containing the extract solution, a first clue of the existence of interaction was deduced by the existence of broadening for several signals in the $^1$H NMR spectrum of the extract.

Figure 8:
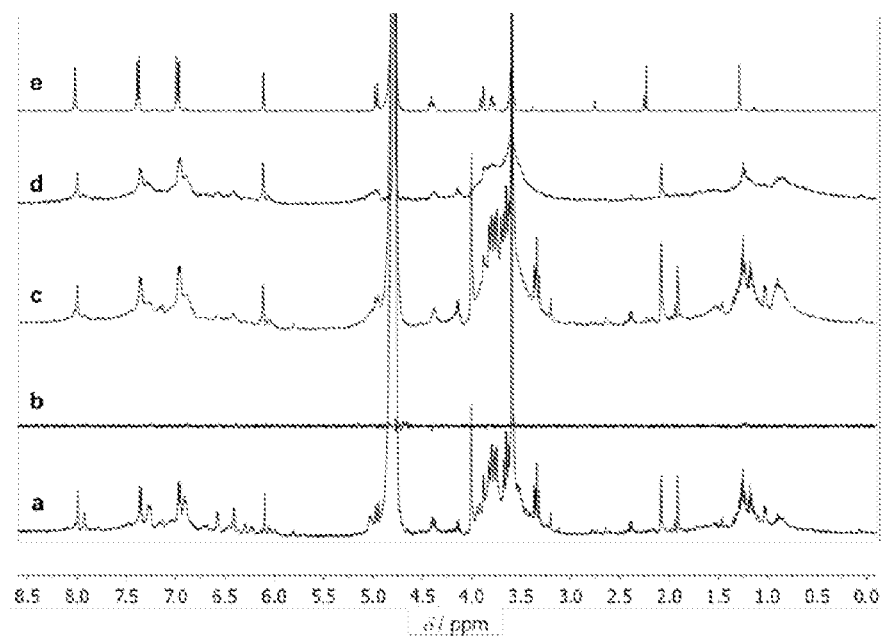
FIG. 8: a) 1H NMR spectrum of the 1.5 mg ethyl acetate extract of G. tenera; b) blank STD-NMR spectrum at 2 s saturation time of the same sample; c) 1H NMR spectrum of the mixture containing Aβ1-42 (80 uM) and 1.5 mg of the ethyl acetate extract of G. tenera; d) STD-NMR spectrum of this mixture at 2 s saturation time; e) 1H NMR spectrum of 2 mM Genistein-8-C-glucoside. All the samples were dissolved in deuterated PBS, pH 7.5, 25° C. The spectrometer frequency was 400 MHz.
Figure 9:
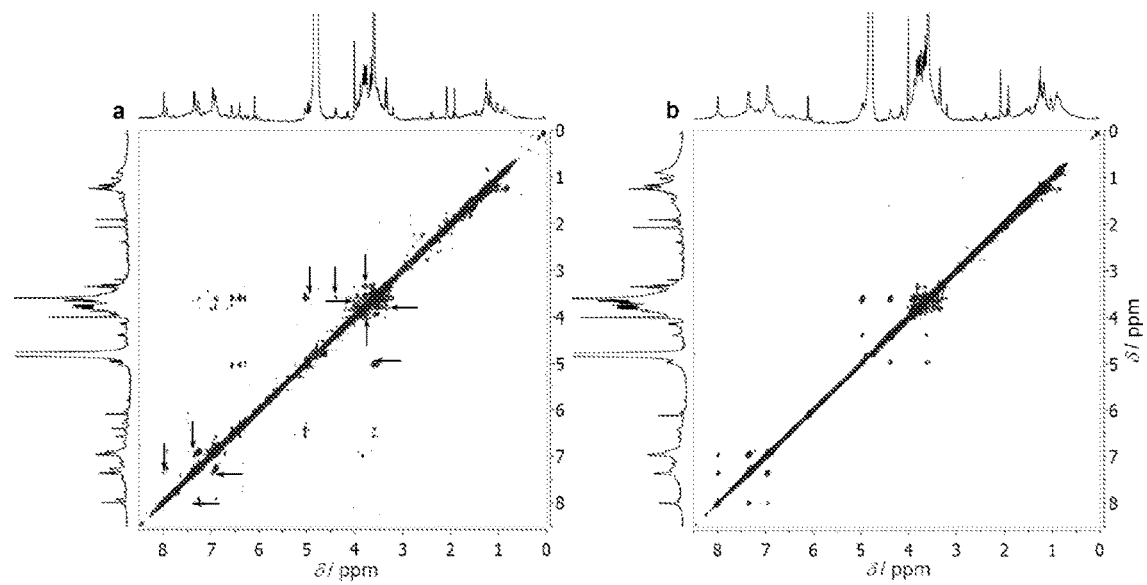
FIG. 9: a) 400 MHz 2D-NOESY spectra of 1.5 mg of the ethyl acetate extract of G. tenera, with a mixing time of 0.8 s. b) trNOESY of the mixture containing Aβ1-42 (80 uM) and 1.5 mg of the extract of G. tenera, with a mixing time 0.3 s. Both samples were dissolved in deuterated PBS, at pH 7.5 and 25° C. The cross peaks in the free state.

Fittingly, the STD spectrum contained several NMR signals, belonging to molecules present into the extract and indicated, in a non-ambiguous manner, the existence of their interactions with the Aβ1-42 oligomers (FIG. 8). Additional evidences of the existence of interaction was deduced from analysis of trNOESY experiments acquired on the same ligand:peptide mixture. The results from this experience reflect an increase of the effective rotational motion correlation time of the molecule in the presence of the AP oligomers, strongly supporting the existence of a binding process of the small molecules present in the extract to the peptide oligomeric state (FIG. 9).

Binding Properties of 8-β-D-Glucopyranosylgenistein

Figure 10:
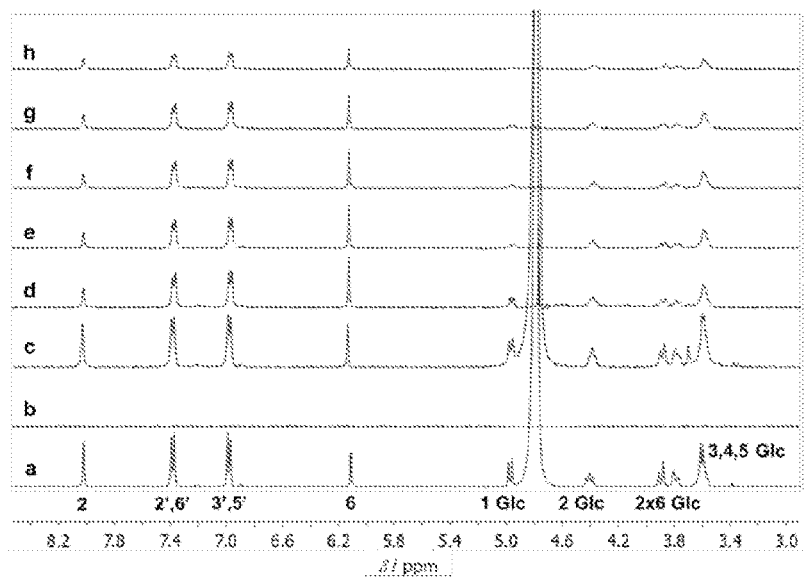
FIG. 10: a) 1H NMR spectrum of 2 mM 8-β-D-glucopiranosylgenistein; b) Blank STD-NMR spectrum of the same sample acquired with a saturation time of 2 s; c) 1H NMR spectrum of the mixture containing 80 uM Aβ1-42 and 2 mM 8-β-D-glucopiranosylgenistein; d-h STD-NMR spectra of the same mixture acquired with different saturation times. (B, 0.5 s; C, 1.2 s; D, 2.0 s; E 3.0 s; F, 5.0 s). Both samples were dissolved in deuterated PBS, pH 7.5, 25° C. The spectra were recorded at 400 MHz. The key resonances are highlighted in spectrum 4a in the bottom part.

The shape of the observed signals in both the STD and trNOESY spectra suggested the presence of 8-β-D-glucopyranosylgenistein, reported as one of the most abundant molecule found in the ethyl acetate extract of G. tenera. To further confirm the interaction of the 8-β-D-glucopyranosylgenistein with the Aβ oligomers, the same NMR experimental protocol was repeated on a mixture containing Aβ1-42 peptide and the pure compound at both 25° C. and 37° C. The results unequivocally demonstrate that 8-β-D-glucopiranosylgenistein is bound to Aβ oligomers. The STD intensities (FIG. 10) clearly indicated that the aromatic aglycone is mostly involved in the binding. Nevertheless, several sugar resonances also appeared, suggesting their participation in the interaction process.

Figure 11:
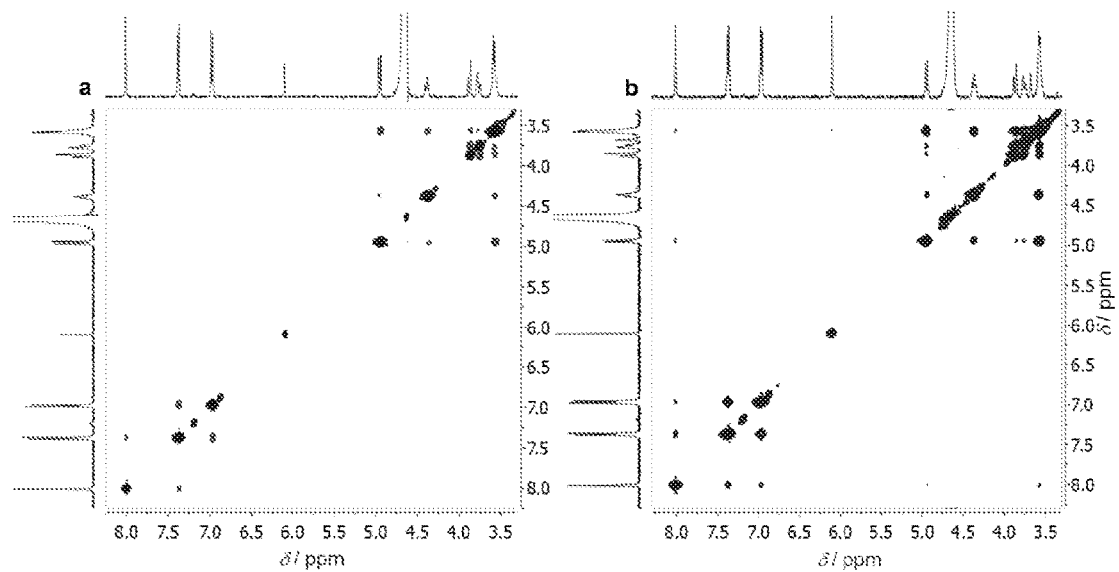
FIG. 11: a) 400 MHz 2D-NOESY spectra of 2 mM 8-β-D-glucopiranosylgenistein with a mixing time of 0.8 s. b) trNOESY of the mixture containing Aβ1-42 (80 uM) and 2 mM 8-β-D-glucopiranosylgenistein, with a mixing time of 0.3 s. Both samples were dissolved in deuterated PBS, at pH 7.5 and 37° C. Positive cross-peak is in red, negative in blue.

An indication of the orientation of the glucoside with respect to the oligomer was deduced from inspection of the trNOESY cross peaks (FIG. 11), which suggests that, in the bound state, the glucoside adopts a preferential conformation in which its α-face points towards H2 at the fused bicyclic moiety of the aglycone.

Figure 14:
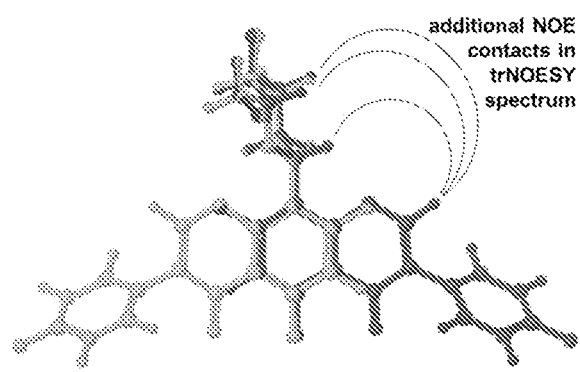
FIG. 14: The two conformations around the glycosidic linkage 8-β-D-glucopiranosylgenistein. The global minimum is shown in violet, while the local minimum is in yellow. NOE experimental contacts are highlighted.

Insights on the actual geometry were obtained by using molecular mechanics (MM) calculations, with the MM3 force field, as implemented in the MacroModel program (Maestro Suite). Two possible conformations around the glycosidic linkage were identified, which only differed in 2.6 kJ/mol. The global minimum (defined by an anti-geometry for the $H1_{Glc}$-$C1_{Glc}$-C8-C7 torsion angle) is shown in violet in FIG. 14, while the alternative local minimum (with a syn orientation) is displayed in yellow.

Binding Properties of Genistein 7-O-Glucoside

Figure 12:
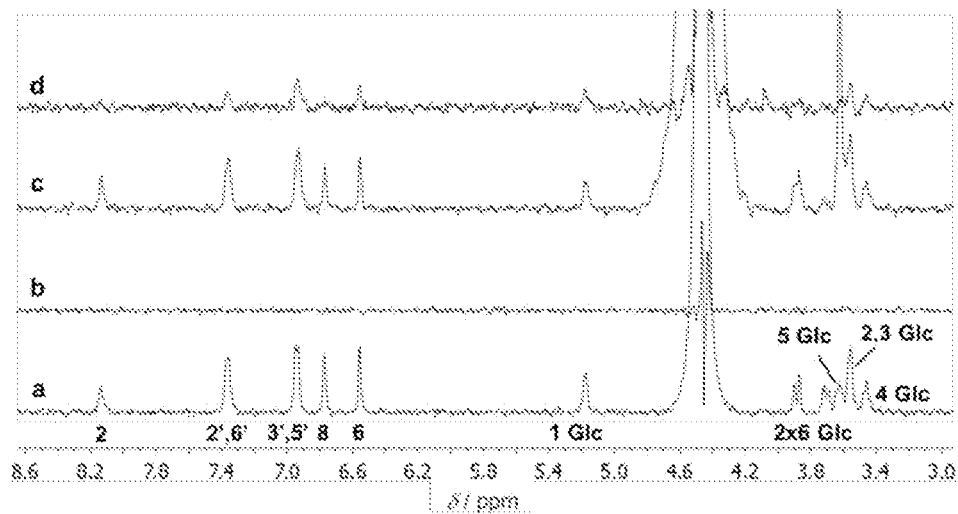
FIG. 12: a) 400 MHz 1H NMR spectrum of 1 mM genistein-7-O-glucoside; b) Blank STD-NMR spectrum of the same sample acquired with a saturation time of 2 s; c) 1H NMR spectrum of the mixture containing 80 uM Aβ1-42 and 1 mM Genistein-7-O-glucoside; d) STD-NMR spectrum of the same mixture acquired with a saturation time of 2 s. Both samples were dissolved in deuterated PBS+5% DMSO, pH 7.5, 50° C.
Figure 15:
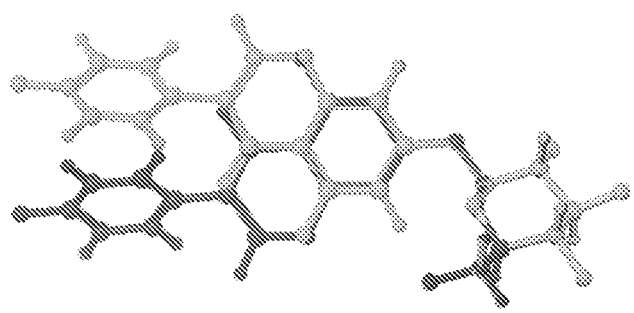
FIG. 15. Superimposition of the possible conformers of genistein-7-O-glucoside according to MM3* calculations. They are basically isoenergetic.
Figure 16:
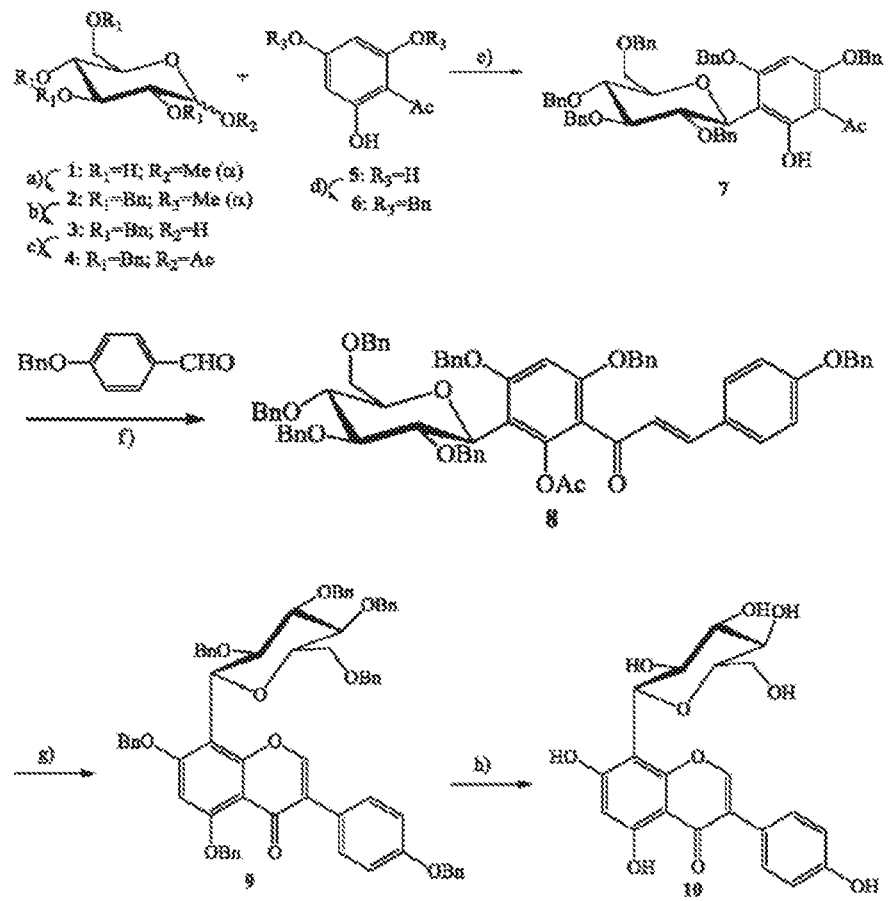
FIG. 16: Synthesis of compounds type A and Benzylation of acetophloroglucinol
Figure 16:
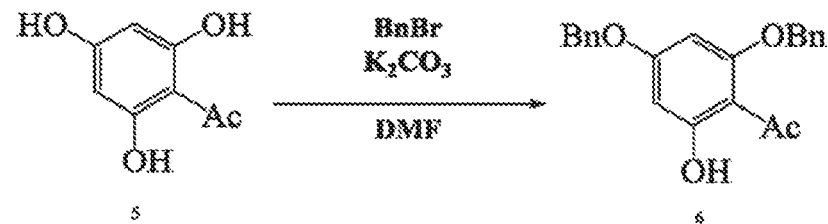

The analysis of a $^1$H-NMR 2D DOSY spectrum acquired on the G. tenera extract at 25° C. allowed to calculate a diffusion coefficient of 2.65±0.035 $10^{-10}$ m$^2$/s for this compound vs. a diffusion coefficient of 3.5±0.02 $10^{-10}$ m$^2$/s found for the genistein-8-C-glucoside, indicating that this new ligand behaves in solution as a larger molecular entity. The STD spectrum obtained allows assessing that also genistein-7-O-glucoside was bound to Aβ1-42 peptide, and supported that this is indeed the second component of G. tenera extract interacting with the oligomeric target (FIG. 12). The existence of broad signals in the extract, as well as its insolubility when pure in PBS, is probably due to the existence of intermolecular stacking among several molecules. Indeed, the conformational search performed with the MM3* force field indicated that this compound may assume two extended iso-energy conformations (FIG. 15), which would easily permit the existence of intermolecular aromatic-aromatic or carbohydrate-aromatic stacking. The formation of a supramolecule would explain the slow diffusion coefficient found for this molecule in the extract solution.

Binding Properties of Genistein

Figure 13:
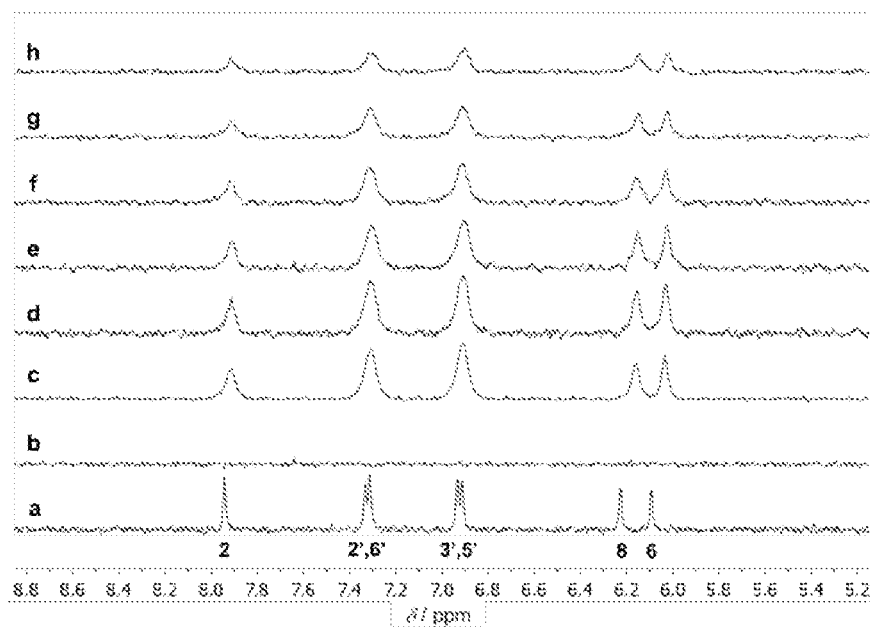
FIG. 13: a) 1H NMR spectrum of 1 mM genistein; b) STD-NMR spectrum of the same sample acquired with a saturation time of 2 s; c) 1H NMR spectrum of the mixture containing 80 uM Aβ1-42 and 1 mM Genistein; d-h STD-NMR spectra of the same mixture acquired with different saturation times. (B, 0.5 s; C, 1.2 s; D, 2.0 s; E 3.0 s; F, 5.0 s). All samples were dissolved in deuterated PBS, at pH 7.5 and 37° C. and recorded at 400 MHz.

Additional STD (FIG. 13) and trNOESY experiments were performed for the genistein aglycone in the presence of the Aβ1-42 peptide oligomers. They also demonstrated that genistein itself is an efficient Aβ oligomer ligand. The results described above prove that this plant is a source of bioactive compounds with a potential anti-amyloid aggregation effect, useful in the therapeutics of diabetes and/or Alzheimer's disease (AD) and Aβ1-42 oligomers seem to act as an in vitro model of type 2 diabetes for this type of compounds, supporting the results obtained for the extract and for 8-β-D-glucosylgenistein in the biological assays with STZ-induced diabetic rats.

The invention claimed is:

1. A method for treating one or more of diabetes and Alzheimer's disease comprising: intraperitoneally administering a composition consisting essentially of 8-β-d-Glucosylgenistein to a diabetic animal model, wherein 8-β-D-Glucosylgenistein has an anti-amyloid aggregation effect.

2. The method of claim 1, wherein said 8-β-D-glucosylgenistein controls the glycaemia on the diabetic animal model, both on the fasting and post-load periods.

3. The method of claim 1, wherein the administration of 8-β-D-Glucosylgenistein is in a dose of 4 mg/kg or less of body weight of the animal model, per day, for seven days, for the return of basal fasting glycaemia and for the return of postload glucose excursions to normal control values on rats made diabetic by prior destruction of pancreatic cells with streptozotocin in an amount of 40 mg/kg.

4. The method of claim 1, wherein said 8-β-D-Glucosylgenistein by itself or by any product of its metabolization, increases glucose-induced insulin secretion, by direct or indirect interaction with pancreatic cells.

5. The method of claim 1, wherein said 8-β-D-Glucosylgenistein by itself or by any product of its metabolization, is able to increase insulin sensitivity, by direct or indirect interaction with peripheral cells.

6. The method of claim 1, wherein said 8-β-D-Glucosylgenistein, consists of a low toxic agent in eukaryotic cells, ten times less toxic than chloramphenicol, when evaluated by the MTT cell viability assay.

* * * * *